(12) United States Patent
Jeong

(10) Patent No.: US 12,037,640 B2
(45) Date of Patent: Jul. 16, 2024

(54) SEQUENCING AN INSERT AND AN IDENTIFIER WITHOUT DENATURATION

(71) Applicant: Agilent Technologies, Inc., Santa Clara, CA (US)

(72) Inventor: Kyeong Soo Jeong, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 544 days.

(21) Appl. No.: 17/144,900

(22) Filed: Jan. 8, 2021

(65) Prior Publication Data

US 2022/0220550 A1 Jul. 14, 2022

(51) Int. Cl.
*C12Q 1/6869* (2018.01)
*C12Q 1/6855* (2018.01)

(52) U.S. Cl.
CPC ......... *C12Q 1/6869* (2013.01); *C12Q 1/6855* (2013.01)

(58) Field of Classification Search
None
See application file for complete search history.

(56) References Cited

U.S. PATENT DOCUMENTS

| | | |
|---|---|---|
| 5,948,902 A | 9/1999 | Honkanen et al. |
| 8,481,292 B2 | 9/2013 | Casbon et al. |
| 2009/0163366 A1* | 6/2009 | Nickerson ............ C12Q 1/6869 506/4 |
| 2013/0012399 A1 | 1/2013 | Myers et al. |
| 2015/0031560 A1* | 1/2015 | Fabani ................. C12Q 1/6874 506/4 |
| 2015/0148239 A1 | 5/2015 | Peter et al. |
| 2015/0197798 A1 | 7/2015 | Xu et al. |
| 2017/0283864 A1 | 10/2017 | Ach et al. |
| 2019/0017113 A1 | 1/2019 | Corioni et al. |
| 2019/0194737 A1 | 6/2019 | Ach et al. |
| 2020/0109397 A1 | 4/2020 | Klass et al. |

FOREIGN PATENT DOCUMENTS

| | | |
|---|---|---|
| WO | 2015073711 A1 | 5/2015 |
| WO | 2017218979 A1 | 12/2017 |
| WO | 2018045109 A1 | 3/2018 |
| WO | 2019209946 A1 | 10/2019 |

OTHER PUBLICATIONS

PCT, "Notification of Transmittal of The International Search Report and Written Opinion" mailed on Apr. 6, 2022, Application No. PCT/US2021/062222, 8 pages.
Illumina, Inc. (2010). Illumina Sequencing Technology; Highest data accuracy, simple workflow, and a broad range of applications. [Brochure]. 5 pages.

\* cited by examiner

*Primary Examiner* — Samuel C Woolwine
*Assistant Examiner* — Carolyn L Greene

(57) ABSTRACT

Methods and kits for next-generation sequencing are disclosed. In some embodiments, the present methods comprise sequencing an insert and sequencing an insert without an intervening denaturation step. Decreased sequencing signal from insert sequences, the use of unlabeled nucleotides to form double stranded insert constructs, and the use of synthesis blocking nucleotides are also discussed.

16 Claims, 5 Drawing Sheets

SEQUENCING AN INSERT AND AN IDENTIFIER WITHOUT DENATURATION

CROSS-REFERENCE TO RELATED APPLICATIONS

None.

FIELD OF THE INVENTION

Methods and kits for next-generation sequencing approaches are disclosed.

BACKGROUND

Next-generation sequencing (NGS) has revolutionized molecular biology, making it significantly faster and less expensive to determine genomic sequences. In order to perform NGS on deoxyribonucleic acid (DNA) and other polynucleotides, the polynucleotides must be prepared for use with the sequencing system, usually by addition of oligonucleotides with known sequences, generally referred to as adaptors. These known adaptors make the polynucleotide compatible with the system, such as by adding sequences that will anneal to complimentary oligonucleotides on a flow cell of the sequencer. The adaptors can contain multiple functional regions, such as a region for attachment to the sequencing instrument, annealing of sequencing primers, and/or indexing of biological samples, i.e., sample barcodes (SBC) or unique molecular barcodes (MBC). SBC and MBC can be sequenced along with the polynucleotide sample of interest unknown DNA sequences (inserts) to identify the biological source and uniqueness the insert, respectively.

Sequencing by synthesis (SBS) systems use four fluorescently labeled nucleotides to sequence the tens of millions of clusters on the flow cell surface in parallel. During each sequencing cycle, a single labeled deoxynucleoside triphosphate (dNTP) is added to the nucleic acid chain. The nucleotide label serves as a terminator for polymerization, so after each dNTP incorporation, the fluorescent dye is imaged to identify the base and then enzymatically cleaved to allow incorporation of the next nucleotide. Since all four reversible terminator-bound dNTPs (A, C, T, G) are present as single, separate molecules, natural competition minimizes incorporation bias. The identification of each nucleotide is made based on from a signal from the label measured during each cycle. The result is a sequencing method that sequentially identifies each nucleotide in a polynucleotide of interest.

In many sequencing-by-synthesis systems, the inserts are sequenced by forming a complementary strand from labeled nucleotides, and then the strand synthesized from this insert sequencing is removed by denaturation. This denaturation step is believed to be necessary since the sequencing signals from inserts are believed to interfere with subsequent sequencing of the identifiers.

In some formats, a polynucleotide such as DNA is affixed to a solid surface in a sequencing system (such as a flowcell, a bead) via one or more adaptors and amplified to increase signal strength. In general, a library is prepared for sequencing by fragmentation of a sample into polynucleotide fragments, with attachment or one or more adaptors to the fragments to form polynucleotide constructs, and amplification of the polynucleotide fragments. The fragments can be amplified with one or more amplification primers. In sequencing-by-synthesis systems, sequencing primers hybridize with primer binding sites on the polynucleotide constructs, and labeled dideoxynucleotides are added enzymatically as the sequencing primer is extended. The signals from the labeled dideoxynucleotides are detected and analyzed to determine the sequence.

A polynucleotide of interest may be analyzed using a single-end or paired-end sequencing method. Single-end sequencing methods involve reading a genomic fragment from one end of the fragment towards the opposite end. A single-end sequencing read provides one read per fragment corresponding to n base pairs of one of the two ends of the fragment, where n is the number of sequencing cycles. Paired-end methods involve reading a nucleic acid fragment from one end to the other end up to a specified read length, and then another round of reading from the opposite side of the fragment. For paired-end methods, a forward sequence read and a reverse sequence read is performed and the data paired into adjoining sequences. The sequences are matched with the reference sample to identify variants.

NGS sequencing systems, such as the ones described above, generally require that previously synthesized strands formed as a result of the addition of labeled nucleotides are denatured (separated from the insert) before starting new primer annealing and sequencing. For example, the complementary strands that are produced as a result of sequencing an insert, are denatured prior to annealing second sequencing primers for sequencing SBCs and/or MBCs. Alternatively, synthesized strands that are produced when sequencing SBCs and/or MBCs are denatured prior to annealing primers for sequencing DNA inserts.

However, denaturation is time-consuming step and may damage DNA insert, potentially introducing the sequencing errors. Accordingly, a sequencing method which does not require denaturation steps would be a useful contribution to the field, particularly if the method has utility in combination with high-throughput sequencing analysis.

SUMMARY OF THE INVENTION

The present disclosure provides methods and kits for next-generation sequencing. The present methods generally comprise sequencing an insert and sequencing an identifier which are present in a polynucleotide construct without an intervening denaturation step, thereby reducing the time required for sequencing, avoiding potential sequencing errors, and/or providing other advantages.

These and other features and advantages of the present invention will be apparent from the following detailed description, in conjunction with the appended claims.

BRIEF DESCRIPTION OF THE DRAWINGS

The present teachings are best understood from the following detailed description when read with the accompanying drawing figures. The features are not necessarily drawn to scale.

DEFINED TERMINOLOGY

Figure 1:
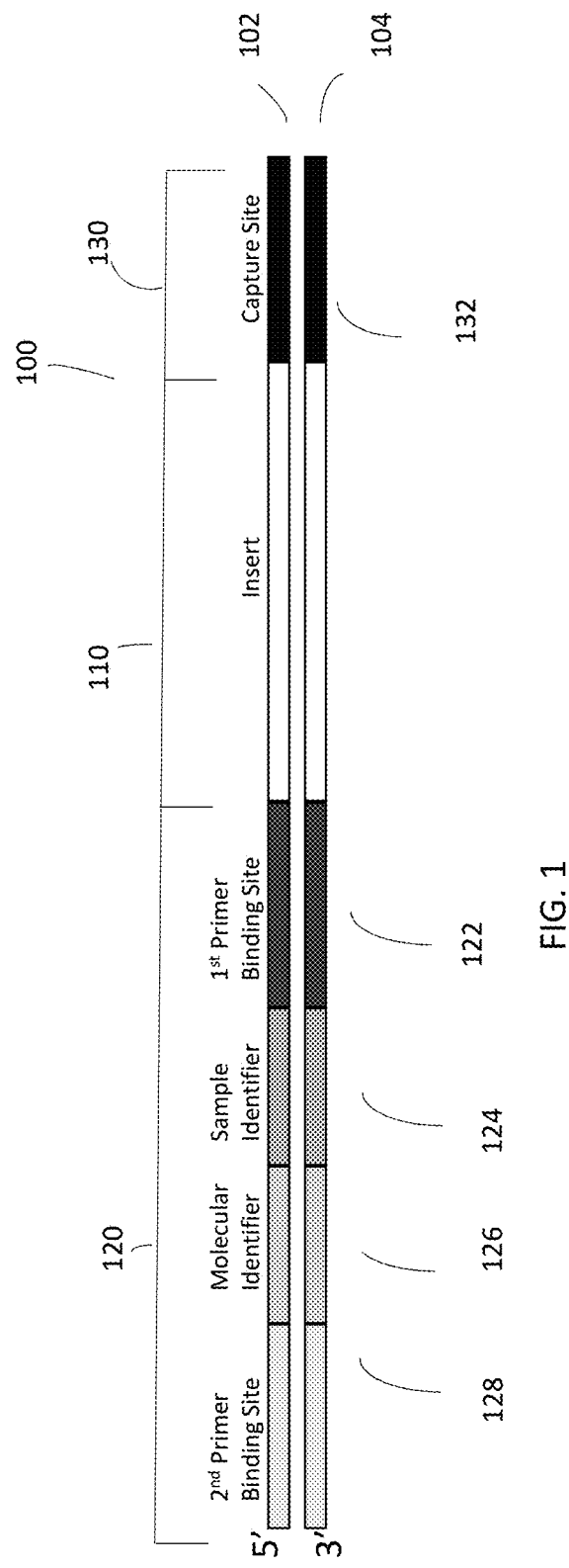
FIG. 1 illustrates an exemplary polynucleotide construct comprising an insert and an adaptor.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

The term "polynucleotide" is used herein to describe a polymer of any length, e.g., greater than about 10 bases, greater than about 100 bases, greater than about 500 bases, greater than 1000 bases, up to about 10,000 or more bases, composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, and thymine (G, C, A, and T, respectively).

The term "nucleoside" as defined herein is a compound including a purine, deazapurine, or pyrimidine base linked to a sugar or a sugar substitute, such as a carbocyclic or acyclic linker at the 1' position or equivalent position and includes 2'-deoxy and 2'-hydroxyl, 2',3'-dideoxy forms, as well as other substitutions.

The term "nucleoside polyphosphate" as used herein refers to a phosphate ester of a nucleoside, with two or more phosphate groups. Adenosine triphosphate and deoxyguanosine pentaphosphate are examples of nucleoside polyphosphates. Nucleoside polyphosphates may contain chemical groups attached to the terminal phosphate or to internal phosphates. For example, nucleoside polyphosphates may include molecules with an electrochemical label, mass tag, charge blockade label, or a chromogenic label, chemiluminescent label, fluorescent dye, or fluorescence quenching label attached to the terminal phosphate or to an internal phosphate in a polyphosphate chain. Further examples of chemical groups that may be used as labels include chromophores, enzymes, antigens, heavy metals, magnetic probes, phosphorescent groups, radioactive materials, scattering or fluorescent nanoparticles, Raman signal generating moieties, and electrochemical detection moieties. Additionally, the term "nucleoside polyphosphate" as used herein refers to a phosphate ester of a nucleoside, which may comprise imido groups or other modifications to the phosphate chain. For example, adenylyl imidophosphate (AMP-PNP) and deoxycytosine 5'-(gamma-thiotriphosphate) and analogues such as ADP.BeF3 are further examples of nucleoside polyphosphates.

The term "nucleotide" as used herein refers to a phosphate ester of a nucleoside, wherein the esterification site typically corresponds to the hydroxyl group attached to the C-5 position of the pentose sugar. In some cases nucleotides comprise nucleoside polyphosphates. However, the terms "added nucleotide," "incorporated nucleotide," "nucleotide added" and "nucleotide after incorporation" all refer to a nucleotide residue that is part of an oligonucleotide or polynucleotide chain.

The terms "nucleoside", "nucleotide", "deoxynucleoside", and "deoxynucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the "nucleoside", "nucleotide", "deoxynucleoside", and "deoxynucleotide" include those moieties that contain not only conventional ribose and deoxyribose sugars, but other sugars as well. Modified nucleosides, nucleotides, deoxynucleosides or deoxynucleotides also include modifications on the sugar moiety, e.g., wherein one or more of the hydroxyl groups are replaced with halogen atoms or aliphatic groups, or are functionalized as ethers, amines, or the like.

Natural nucleotides or nucleosides are defined herein as adenine (A), thymine (T), guanine (G), and cytosine (C). It is recognized that certain modifications of these nucleotides or nucleosides occur in nature. However, modifications of A, T, G, and C that occur in nature that affect hydrogen bonded base pairing are considered to be non-naturally occurring. For example, 2-aminoadenosine is found in nature, but is not a "naturally occurring" nucleotide or nucleoside as that term is used herein. Other non-limiting examples of modified nucleotides or nucleosides that occur in nature that do not affect base pairing and are considered to be naturally occurring are 5-methyl cytosine, 3-methyladenine, O(6)-methylguanine, and 8-oxoguanine, etc. Nucleotides include any nucleotide or nucleotide analog, whether naturally-occurring or synthetic. Exemplary nucleotides include phosphate esters of deoxyadenosine, deoxycytidine, deoxyguanosine, deoxythymidine, adenosine, cytidine, guanosine, and uridine. Other nucleotides include an adenine, cytosine, guanine, thymine base, a xanthine or hypoxanthine, 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or by being capable of base-complementary incorporation, and includes chain-terminating analogs. A nucleotide corresponds to a specific nucleotide species if they share base-complementarity with respect to at least one base.

In addition to purines and pyrimidines, modified nucleotides or analogs, as those terms are used herein, include any compound that can form a hydrogen bond with one or more naturally occurring nucleotides or with another nucleotide analog. Any compound that forms at least two hydrogen bonds with T or with a derivative of T is considered to be an analog of A or a modified A. Similarly, any compound that forms at least two hydrogen bonds with A or with a derivative of A is considered to be an analog of T or a modified T. Similarly, any compound that forms at least two hydrogen bonds with G or with a derivative of G is considered to be an analog of C or a modified C. Similarly, any compound that forms at least two hydrogen bonds with C or with a derivative of C is considered to be an analog of G or a modified G. It is recognized that under this scheme, some compounds will be considered for example to be both A analogs and G analogs (purine analogs) or both T analogs and C analogs (pyrimidine analogs).

As used herein, the term "polynucleotide construct" refers to a polynucleotide that is ligated or otherwise attached to another nucleic acid, such as an adaptor. For example, a polynucleotide construct may contain a DNA insert to be sequenced, a capture site for flow cell attachment, identifier DNA sequences such as SBC and MBC, and primer binding sites for a first and second primer.

As used herein, the term "insert" refers to a polynucleotide of interest, which may be desired for sequencing and/or other analysis. An insert may be present in a polynucleotide construct, to be sequenced by NGS. An insert may be single-stranded or double-stranded, and often is double-stranded DNA when attached to an adaptor to form a polynucleotide construct. "DNA insert," as used herein, can refer to a specific sequence or the complement thereof or to both. A DNA insert may contain a target sequence. A "target sequence" may be within a nucleic acid in vitro or in vivo within the genome of a cell, which may be any form of single-stranded or double-stranded nucleic acid.

As used herein, the term "capture site" refers to a nucleic acid sequence configured for attachment of a polynucleotide construct to a flow cell or other surface, for NGS sequencing or other analysis processing.

As used herein, the term "identifier" refers to a nucleic acid sequence that can be used to identify a particular polynucleotide construct. An "identifier" may be a "sample barcode" or "SBC" sequence for identifying a particular biological sample. An "identifier" may also refer to a "molecular barcode" for identification of unique molecules present in the sample. Also, an "identifier" may contain both an SBC and an MBC.

As used herein, the term "primer binding site" refers to a site within an oligonucleotide or polynucleotide configured for hybridizing to a primer, so that adjacent sequences can be amplified or sequenced such as by primer extension. Primer binding sites are generally adjacent to the 3' end of the sequence for which they are designed to provide sequencing data. Accordingly, sequencing primers generally bind to primer binding sites adjacent to an insert so that nucleotides that are complementary to the insert to be sequenced are added to the 3' end of the sequencing primer. A primer binding site can be a sequence that occurs in a polynucleotide of interest or a sequence that is added to a polynucleotide by adding an adaptor comprising the primer binding site. An adaptor containing a primer binding site can be added by ligation, by use of a transposase, by primer extension, or by other techniques.

"Hybridization" or "hybridizing" refers to a process where completely or partially complementary nucleic acid strands come together under specified hybridization conditions to form a double-stranded structure or region in which the two constituent strands are joined by hydrogen bonds. Although hydrogen bonds typically form between adenine and thymine or uracil (A and T or U) or cytosine and guanine (C and G), other base pairs may form (e.g., Adams et al., "The Biochemistry of the Nucleic Acids," 11th ed., 1992).

The term "primer" means an oligonucleotide that is capable, upon forming a duplex with a polynucleotide template (such as a primer binding site), of acting as a point of initiation of nucleic acid synthesis and being extended from its 3' end along the template so that an extended duplex is formed. The sequence of nucleotides added during the extension process is determined by the sequence of the polynucleotide template. A primer serves as an initiation point for nucleotide polymerization catalyzed by either DNA polymerase, RNA polymerase, or reverse transcriptase. A primer, either enzymatically made or synthetic, may be 4-1000 bases or more in length, e.g., 10-500 bases.

As used herein, the term "primer extension" refers to extension of a primer by annealing specific nucleotides to the 3' end of a primer using a polymerase.

The term "adaptor" refers to a nucleic acid molecule attached to a polynucleotide of interest to form a synthetic polynucleotide, or polynucleotide construct. An adaptor can be single stranded or double stranded, and it can comprise DNA, RNA, and/or artificial nucleotides. An adaptor can be located at an end of a polynucleotide of interest, or it can be located in a middle or interior portion. The adaptor can add one or more functional regions to the polynucleotide construct, such as providing a primer binding site for amplification or sequencing or adding an identifier. By way of example, adaptors can include a first primer binding site, an identifier, such as an SBC and/or MBC, a second primer binding site, and a capture site. Adaptors can also include a universal primer and/or a universal priming site, including a priming site for sequencing. By way of further example, adaptors can contain one or more barcodes of various types or for various purposes, such as molecular barcodes, sample barcodes and/or target-specific barcodes.

The term "sequencing" refers to determining the identity of one or more nucleotides, i.e., whether a nucleotide is a G, A, T, or C.

The term "obtaining a duplex" refers to a duplex made by, for example: a) hybridizing one nucleic acid (e.g., an oligonucleotide) to another, b) extending a primer that is hybridized to a nucleic acid using the nucleic acid as a template (thereby converting a first duplex that has a first primer into a second duplex that comprises an extended primer) or c) nicking a longer double stranded molecule and then removing nucleotides from the nick site using an exonuclease.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

In the present disclosure, numeric ranges are inclusive of the numbers defining the range. It should be recognized that chemical structures and formula may be elongated or enlarged for illustrative purposes.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.7 to 1.15. For example, "approximately the same" means that one of ordinary skill in the art considers the items being compared to be the same.

As used in the specification and appended claims, the terms "a", "an," and "the" include both singular and plural referents, unless the context clearly dictates otherwise. Thus, for example, "a primer" includes one primer and plural primers. In the present disclosure, ordinal numbers such as terms first, second, third, and so on do not mean that a first event occurs before a second event (unless the context indicates otherwise); instead they are used to distinguish different events from each other. A method or kit having first and second elements can also include a third, a fourth, a fifth, and so on, unless otherwise indicated.

As disclosed herein, a number of ranges of values are provided. It is understood that each intervening value between the upper and lower limits of that range is also specifically disclosed. Where the stated range includes one or both of the limits, ranges excluding either or both of those included limits are also included in the invention.

All patents and publications referred to herein are expressly incorporated by reference. The citation of any publication is for its disclosure prior to the filing date and should not be construed as an admission that the present claims are not entitled to antedate such publication. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

DETAILED DESCRIPTION

The present technology provides methods for sequencing that reduce or avoid the use of denaturation between sequencing an insert and an identifier present in a polynucleotide construct. FIG. 1 illustrates an exemplary polynucleotide construct 100 comprising an insert and two identifiers which may be sequencing by the present methods. Of course it is contemplated that other arrangements of polynucleotide constructs can also be employed in the present methods.

More particularly, FIG. 1 shows an exemplary polynucleotide construct 100 comprising an insert 110 and adaptors 120, 130 attached at each end of the insert 110. The polynucleotide construct 100 comprises a top strand 102 and a bottom strand 104, though for many sequencing systems, the strands 102, 104 will be separated prior to introduction to the sequencing instrument. Either or both strands 102, 104 may be used for sequencing, though the bottom strand 104 is more readily used with many sequencing systems due to the 3' to 5' positioning of primer binding sites with respect to identifiers and insert. Insert 110 can be any polynucleotide of interest, and adaptors 120, 130 are attached to facilitate next-generation sequencing of the insert 110. The adaptor 120 comprises several functional regions to facilitate sequencing, such as a first primer binding site 122, to which to a sequencing primer will bind in order to sequence the insert 110. Adaptor 120 also comprises a sample identifier 124, a molecular identifier 126, and a second primer binding site 128. A second sequencing primer will bind to the second primer binding site 128 in order to sequence the molecular identifier 126 and the sample identifier 124. By adding first and second sequencing primers to the sequencing system at different times, a user determines whether the system will perform sequencing on the insert 110 or the identifiers 124, 126. Adaptor 130 comprises a capture site 132, which will attach the polynucleotide construct 100 to a support in a sequencing system (such as a flow cell having primers complementary to the capture site 132). Thus, the exemplary polynucleotide construct 100 includes a capture site for flow cell attachment, a DNA insert to be sequenced, DNA identifier sequences including molecular and sample identifiers to be sequenced, and primer binding sites for first and second sequencing primers adjacent to the insert and identifier sequences, respectively. However, it is contemplated that other arrangements of polynucleotide constructs may also be used with the present methods and kits, such as polynucleotide constructs comprising only one adaptor, or comprising adaptor(s) with additional functional regions or fewer functional regions.

The insert can be any polynucleotide whose sequence is of interest, including genomic DNA (gDNA), complementary DNA (cDNA) derived from a RNA template (e.g., messenger RNA (mRNA) or microRNA (microRNA)), mitochondrial DNA (mtDNA), RNA such as mRNA, microRNA, and other polynucleotides. The insert can be of any origin, such as microbial, viral, fungal, plant, or mammalian. The insert may be of any suitable base length, which will generally be selected based on the sequencing system to be used.

The insert may be obtained by any suitable mechanism. In some embodiments, a sample comprising genomic DNA is fragmented using any suitable technique such as by physical fragmentation, enzymatic fragmentation, or chemical shearing fragmentation. In some embodiments, the polynucleotide is fragmented using a physical fragmentation method such as sonication, acoustic shearing, or hydrodynamic shearing. In some embodiments, the polynucleotide is fragmented using a restriction enzyme. In some embodiments, the polynucleotide is fragmented using an enzyme such as DNase I or a transposase. In some embodiments, the polynucleotide is fragmented using a chemical shearing method such as heat digestion in the presence of a metal cation. In some embodiments, the polynucleotide is randomly fragmented. In some embodiments the polynucleotide can be treated with sodium bisulfite or other chemical modifiers. In some embodiments, the polynucleotide fragments are used to populate a sequencing library.

In some embodiments, the insert has a base length of at least about 30, about 50, about 70, about 100, or longer, or a base length of at most about 2,000, about 1,000, about 800, about 500, about 200, about 120, or shorter. Any of the foregoing minimums and maximums can be combined to form a range for the base length of the insert.

Various adaptors are known in the field and can be used or modified for use in the present methods and kits. For instance, suitable adaptors include Y adaptors which can be attached to polynucleotides to produce libraries with varying 5' ends. The adaptors may be separate sequences (for example AB adaptors) in which an A adaptor is attached to one end of a polynucleotide and a B adaptor is attached to an opposite end of the polynucleotide. The adaptors may be stem-loop adaptors, in which a hairpin loop is attached to an end of the polynucleotide; a portion (typically the stem) can be cleaved before amplification or sequencing. An adaptor can be attached to an insert by any suitable technique, including, but not limited to ligation, use of a transposase, hybridization, and/or primer extension. For example, adaptors may be ligated to ends of the insert, usually after preparing the insert for ligation, such as by end-repairing and polishing. As another example, adaptors can be attached by using a transposase to insert transposons comprising adaptors into a polynucleotide, thereby providing adaptors at the ends of inserts formed from the polynucleotide.

In some embodiments, a polynucleotide construct comprises, consists essentially of, or consists of a primer binding site for sequencing an identifier, one or more identifiers, a primer binding site for sequencing an insert, an insert, and optionally a capture site. The polynucleotide construct can be provided as a single-stranded molecule, a double-stranded molecule, or as a molecule having a single-stranded portion and a double-stranded portion. In some embodiments, the identifier comprises a sample identifier, or a molecular identifier, or both. In some embodiments, the insert comprises a 5' end and a 3' end, and a primer binding site is contiguous with one of the ends of the insert. In some embodiments, a primer binding site is contiguous with a sample identifier or a molecular identifier. In some embodiments, a single-stranded polynucleotide construct comprises, consists essentially of, or consists of (in 5' to 3' order or in 3' to 5' order) a primer binding site for sequencing an identifier, one or more identifiers, a primer binding site for sequencing an insert, an insert, and optionally a capture site.

In some embodiments, the present methods leverage the decrease in signal intensity that occurs after a number of sequencing cycles in some systems. For instance, in some sequencing-by-synthesis systems, the labeled nucleotides are added one-by-one to strands complementary to inserts in the sequencing cycles. As the cycles progress, the signal produced from the labels decreases in intensity. It has been found that, after about seventy sequencing cycles in which a first primer is extended, the signal produced as subsequent labeled nucleotides are added can be ignored or discounted if sequencing begins with a second primer. That is, the signal from a second primer being extended for identifier sequencing will be distinguishably stronger than the signal from the first primer extension. Accordingly, the second primer can be extended to sequence the identifier, even while continuing to extend the first primer and without denaturing the strand complementary to the insert.

Figure 2:
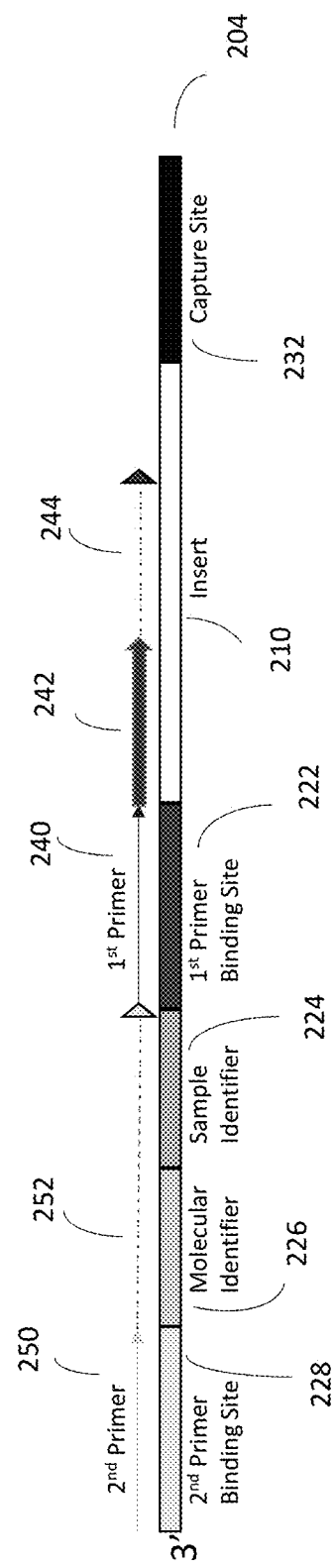
FIG. 2 illustrates an embodiment of the present sequencing methods wherein labeled nucleotides are added to the first primer, forming a double-stranded insert portion, and the double-stranded insert portion is not denatured prior to identifier sequencing.

For example, as shown in FIG. 2, an insert can be sequenced initially from a first sequencing primer for a desired number of sequencing cycles. FIG. 2 illustrates an embodiment of the present sequencing methods in which a strand 204 comprising an insert 210, a sample identifier 224, and a molecular identifier 226 are sequenced. Strand 204 is attached to a surface in a sequencing instrument by its capture site 232. A first primer 240 binds to first primer binding site 222 in order to sequence the insert 210. As labeled nucleotides are added by primer extension, a strand 242 complementary to the insert 210 results, thereby forming a double-stranded insert portion. After a number of sequencing cycles are performed (for example, at least 70 sequencing cycles, thereby forming a complementary strand 242 of approximately 70 nucleotides), a second primer 250 is provided to the sequencing system (e.g., to the flow cell where the polynucleotide is being sequenced). The second primer 250 binds to a second primer binding site 228 and is extended by addition of labeled nucleotides. Thus, the identifiers 224, 226 are sequenced, forming a double-stranded identifier portion 252. The second primer 250 is extended and the identifiers are sequenced without an intervening denaturation step that separates complementary strand 242 from insert 210. The signal produced by labeled nucleotides 244 being added to the complementary strand 242 is sufficiently decreased prior to addition of the second sequencing primer such that the decreased signal has a negligible effect on the new identifier sequencing signal from double-stranded identifier portion 252. In some embodiments, at least 30, 35, 40, 45, 50, 55, 60, 65, 70, 75, 80, 85, 90, 95, 100 or more insert sequencing cycles are performed before performing adding the second primer or identifier sequencing cycles. In some embodiments, the sequencing system determines whether a signal level from the insert sequencing is at or below a threshhold before the second primer is added. In some embodiments, the sequencing system detects an insert signal level from the insert sequencing prior to adding the second primer, and adjusts an interpretation of a detected identifier signal level based on the insert signal level.

In some embodiments, the present technology provides methods for sequencing a polynucleotide construct without a denaturation step. In some embodiments, the polynucleotide construct comprises an insert and an identifier. In some embodiments, the insert is sequenced by annealing a first primer to the polynucleotide construct at a primer binding site that is 3' to the insert. The method also comprises extending the first primer by addition of labeled nucleotides complementary to the insert, and detecting the added labeled nucleotides to determine a sequence of the insert, wherein the extension of the first primer forms a double-stranded insert portion comprising the insert and a strand complementary to the insert. In some embodiments, the identifier is then sequenced by annealing a second primer the polynucleotide construct at a primer binding site that is 3' to the identifier, extending the second primer by addition of labeled nucleotides complementary to the identifier, and detecting the added labeled nucleotides to determine a sequence of the identifier.

In some embodiments, the present methods comprise extending the double-stranded insert portion after the addition of the labeled nucleotides by continuing to extend the strand complementary to the insert until substantially all of insert is double stranded. The extension of the strand can be continued with unlabeled nucleotides rather than labeled nucleotides complementary until the complementary strand extends substantially entirely over the insert. Thus, in some embodiments of the present methods, a first primer is used with labeled nucleotides to sequence an insert, and then unlabeled nucleotides (for example, natural nucleotides (A, G, T, and C) without fluorescent labels or other modifications) are added to the sequencing reaction to complete synthesis for the remaining insert. Unlike labeled nucleotides utilized in some NGS platforms, unlabeled nucleotides (which may be natural nucleotides) can be incorporated without any additional chemical steps or DNA polymerase mutants. Once the unlabeled nucleotides have been added to form a strand complementary to the entire insert sequence, thereby forming a double stranded insert portion, there is no insert remaining for additional nucleotide additions to the insert. Then, a second sequencing primer is annealed to a second priming site and labeled nucleotides are added in order to sequence the identifier. Thus, denaturation is not necessary for sequencing the identifier(s) (e.g., MBC and/or SBC) because there is no other single stranded insert remaining to be extended. In some embodiments, this approach is also desirable because the use of unlabeled natural nucleotides has a minimal impact on subsequent sequencing steps.

Figure 3:
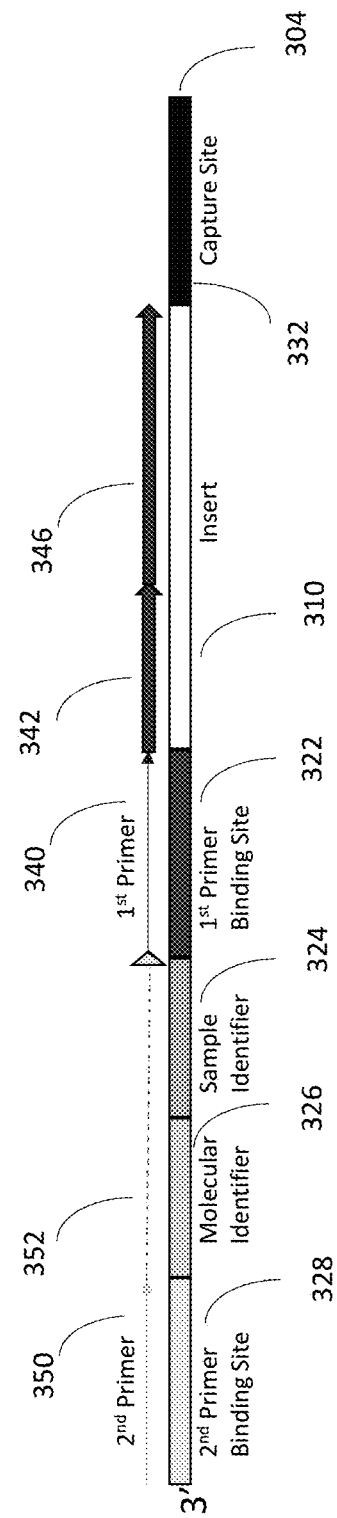
FIG. 3 illustrates an embodiment of the present sequencing methods wherein labeled nucleotides are added to the first primer for insert sequencing and then unlabeled nucleotides are added prior to identifier sequencing.

FIG. 3 illustrates some embodiments of the present sequencing methods in which a strand 304 comprising an insert 310, a sample identifier 324, and a molecular identifier 326 are sequenced. Strand 304 is attached to a surface in a sequencing instrument by its capture site 332. A first primer 340 binds to first primer binding site 322 in order to sequence the insert 310. As labeled nucleotides are added by primer extension, a strand 342 complementary to the insert 310 results, thereby forming a double-stranded insert portion. A desired number of sequencing cycles are performed (for example, at least 30, 35, 40, 45, 50, 55, 60, 65, 70, 75, 80, 85, 90, 95, 100 or more sequencing cycles), thereby forming a complementary strand 342 by extending the first primer 340. After the desired number of sequencing cycles, unlabeled nucleotides are added to the sequencing reaction, and primer extension continues with a strand 346 that extends over a desired length of the insert 310, such as substantially all of the insert 310. Optionally the labeled nucleotides are removed prior to adding of the unlabeled nucleotides. In some embodiments, the addition of unlabeled nucleotides proceeds much more rapidly than addition of labeled nucleotides, due to the absence of a label and/or the absence of detecting a label. After forming a double-stranded insert portion comprising substantially all (or another desired length) of the insert 310, a second primer 350 is added which binds to a second primer binding site 328. The second primer 350 is extended by addition of labeled nucleotides and the identifier is sequenced, thereby forming a double-stranded identifier portion 352. Because strand 346 occupies a desired length of the insert 310, the labeled nucleotides cannot hybridize to the insert 310 and will not produce a signal.

In some embodiments, the present methods comprise adding one or more blocking nucleotide to the double-stranded construct portion after the addition of the labeled nucleotides. In such embodiments, once the insert has been sequenced for a sufficient number of sequencing cycles, insert sequencing can be blocked by addition of 3'-deoxynucleotides or other polymerization-blocking nucleotides for another cycle. 3'-deoxynucleotides can be added to the 3' end of the strand and block any further addition of nucleotides due to the absence of the 3'-OH group. Other examples of blocking nucleotides are 2',3'-dideoxynucleotides, Acyclonucleotide, and others. After the strand from extending the first primer is blocked, a second sequencing primer can be annealed to the second primer binding site to sequence the identifier.

Figure 4:
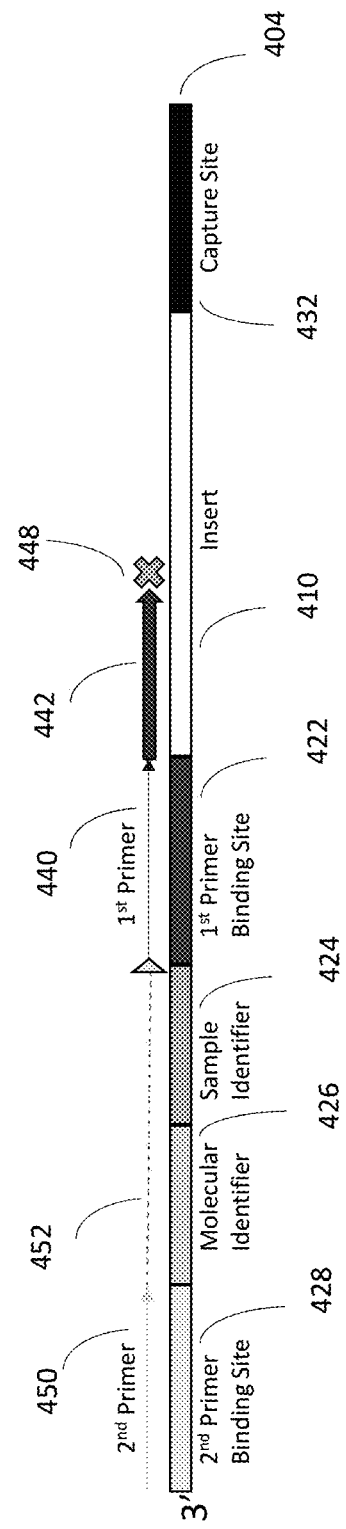
FIG. 4 illustrates an embodiment of the present sequencing methods wherein labeled nucleotides are added to the first primer for insert sequencing and then a blocking nucleotide is added to stop insert sequencing prior to identifier sequencing.

FIG. 4 illustrates some embodiment of the present sequencing methods in which a strand 404 comprising an insert 410, a sample identifier 424, and a molecular identifier 426 are sequenced. Strand 404 is attached to a surface in a sequencing instrument by its capture site 432. A first primer 440 binds to first primer binding site 422 in order to sequence the insert 410. As labeled nucleotides are added by primer extension, a strand 442 complementary to the insert 410 results, thereby forming a double-stranded insert portion. A desired number of sequencing cycles are performed (for example, at least 30, 35, 40, 45, 50, 55, 60, 65, 70, 75, 80, 85, 90, 95, 100 or more sequencing cycles), thereby forming a complementary strand 442 by extending the first primer 440. After the desired number of sequencing cycles, one more blocking nucleotides 448 are added to the sequencing reaction, and primer extension forming strand 442 ceases. The labeled nucleotides need not be removed prior to adding of the blocking nucleotide. Generally any remaining blocking nucleotides which have not been incorporated at the end of strand 442 are is removed from the flow cell prior to addition of a second primer 450 and additional labeled nucleotides for identifier sequencing. Second primer 450 binds to the second primer binding site 428. The second primer 450 is extended by addition of labeled nucleotides and the identifier is sequenced, thereby forming a double-stranded identifier portion 452.

In some embodiments of the present sequencing methods, the first sequencing primer and first primer binding site provide sequencing data from the identifier (SBC and/or MBC) while the second sequencing primer and second primer binding site provides sequencing data from the insert without denaturation steps between sequencing the identifier and sequencing the insert. Thus, the present technology provides methods for sequencing a polynucleotide construct without a denaturation step between the sequencing of the identifier and the sequencing of the insert. In some embodiments, the polynucleotide construct comprises an insert and an identifier. In some embodiments, the identifier is sequenced by annealing a first primer to a region of the polynucleotide construct that is 3' to the identifier, extending the first primer by addition of labeled nucleotides complementary to the identifier, and detecting the added labeled nucleotides to determine a sequence of the identifier, wherein the extension of the first primer forms a double-stranded identifier portion comprising the identifier and a strand complementary to the identifier. In some embodiments, the insert is then sequenced by annealing a second primer to a region of the polynucleotide construct that is 3' to the insert, extending the second primer by addition of labeled nucleotides complementary to the insert, and detecting the added labeled nucleotides to determine a sequence of the insert.

In some embodiments, the method comprises extending the first primer for a desired period or length, and thereby sequencing the identifier, before annealing the second primer to the polynucleotide construct. In some embodiments, the method comprises ligating the strand complementary to the identifier to the second primer before extending the second primer.

In some embodiments, the present methods comprise sequencing an identifier of a polynucleotide construct with a first primer, then extending the double-stranded identifier portion by adding unlabeled nucleotides complementary to the identifier until the complementary strand extends over substantially all of the identifier or over a desired portion of the identifier.

In some embodiments, the present methods comprise sequencing an identifier of a polynucleotide construct with a first primer, then adding a blocking nucleotide to the double-stranded identifier portion before the addition of the second primer and labeled nucleotides and the sequencing of the insert. In some embodiments, the blocking nucleotides are 2',3'-dideoxynucleotides.

As another aspect of the present technology, kits are provided for performing the present sequencing methods, as described above. A kit for sequencing a polynucleotide of interest comprises one or more adaptors; one or more primers; labeled nucleotides; and one or both of (a) unlabeled nucleotides; and (b) blocking nucleotides. In some embodiments, the blocking nucleotides are dideoxy nucleotides. In some embodiments, the kit further comprises a pair of primers that are complementary to or the same as sequences present in one or more adaptors. The kits may additionally comprise suitable reaction reagents (e.g., buffers etc.) for performing a DNA preparation, amplification or sequencing method. The various components of the kit may be present in separate containers or certain compatible components may be precombined into a single container, as desired. For example, in some embodiments, primers and labeled nucleotides may be in a mix, i.e., in a single container. In addition to the reagents described above, a kit may contain any of the additional components used in the method described above, e.g., one or more enzymes and/or buffers, etc.

In some embodiments, the present methods and kits are used to detect the presence, location, or absence of a mutation, such as a single nucleotide polymorphism (SNP) or a genomic rearrangement in a polynucleotide of interest. In some embodiments, the present methods comprise single-end sequencing or paired-end sequencing of the polynucleotide construct.

The present methods comprise sequencing a first and second primer extension in the same direction. The combined sequence data from the first and second primer extensions facilitates read alignment and identification of the insert and of mutations in the insert. The combination of the reads generated in the same direction allow for more accurate identification.

The present methods may be used as part of a high-throughput sequencing method such as a Next Generation Sequencing (NGS) method. In some embodiments, a high-throughput sequencing method comprises three steps: library preparation, immobilization, and sequencing. A polynucleotide sample generally is subjected to fragmentation, and adaptors are attached to one or both ends of the fragments to form a sequencing library. The adaptors may be linear adaptors, circular adaptors, or bubble adaptors. The sequencing library molecules are immobilized on a solid support, and sequencing reactions are performed to identify the polynucleotide sequence. The high-throughput sequencing method may employ Emulsion PCR, Bridge-PCR, or Rolling Circle amplification to provide colonies or copies of the original polynucleotide construct.

Polymerases tend to make errors during PCR (most frequently mis-incorporation of nucleotides) and, if these errors occur during early cycles they appear as variants in the analysis of sequencing data. Molecular identifiers can be used to distinguish PCR errors from actual variants in an insert. The concept of molecular barcodes is that each polynucleotide in a pool to be amplified is attached to a unique molecular identifier. Sequence reads that have different molecular identifiers represent different original inserts, while reads that have the same identifiers are the result of PCR duplication from the same original insert. Molecular barcodes called degenerate base regions (DBR) are disclosed in U.S. Pat. No. 8,481,292 (Population Genetics Technologies Ltd.). The DBRs are random sequence tags that are attached to molecules that are present in the sample. DBRs and other molecular barcodes allow one to distinguish PCR errors during sample preparation from mutations and other variants that were present in the original polynucleotide.

As discussed above, many embodiments of the present method comprise attaching one or more adaptors to an insert to form a polynucleotide construct. An adaptor can be attached to an insert before or after amplification, and in some embodiments the polynucleotide construct is a polynucleotide amplicon. The adaptor can be attached by any suitable technique, such as by ligation, use of a transposase, hybridization, and/or primer extension. In some embodiments, the insert is ligated with an adaptor at one or both ends. In a ligation reaction, a covalent bond or linkage is formed between the termini of two or more nucleic acid molecules (such as an insert and an adaptor). The nature of the bond or linkage may vary, and the ligation may be carried out enzymatically or chemically. Ligations are usually carried out enzymatically to form a phosphodiester linkage between a 5' carbon of a terminal nucleotide of one polynucleotide or oligonucleotide with 3' carbon of another polynucleotide or oligonucleotide. In some embodiments, the adaptor is a Y adaptor which can generate libraries with varying 5' ends and having P5 and P7 priming sites suitable for using on Illumina MiniSeq, NextSeq, and HiSeq 3000/4000 sequencing instruments.

In some embodiments, the present method comprises amplifying an insert, before and/or after it is attached to an adaptor. In some embodiments, an adaptor is located at a 5'-end of a sequence of interest in the polynucleotide, and the adaptor provides a priming site for amplification of the sequence of interest. The adapted polynucleotide is amplified using a first amplification primer and a second amplification primer. The first amplification primer has sequence specificity for a target sequence in the polynucleotide, and is capable of hybridizing to a portion of the target sequence (a polynucleotide of interest). The second amplification primer is capable of hybridizing to a priming site of the adaptor or to a target-specific priming site of the polynucleotide of interest. During the amplification step, the first amplification primer hybridizes to the target sequence and the second primer hybridizes to the sequence priming site on the adaptor. In some embodiments, the first amplification primer hybridizes at the 5'-end of the adapted polynucleotide. The primers of the present method should be sufficiently large to provide adequate hybridization with the target sequence of the insert.

An insert may be amplified using any suitable method. In some embodiments, the insert is amplified using polymerase chain reaction (PCR). In general, PCR comprises denaturation of polynucleotide strands (e.g., DNA melting), annealing of primers to the denatured polynucleotide strand, and extension of primers with a polymerase to synthesize the complementary polynucleotide. The process generally requires a DNA polymerase, forward and reverse primers, deoxynucleoside triphosphates, bivalent cations, and a buffer solution. In some embodiments, the insert is amplified by linear amplification. In some embodiments, the insert is amplified using Emulsion PCR, Bridge-PCR, or Rolling Circle amplification. The amplified insert may be analyzed to determine the order of base pairs using a suitable sequencing method.

In some embodiments, one or more of inserts, polynucleotide constructs, and/or primers are immobilized on a solid support. Immobilization of the amplification primer and/or inserts can facilitate washing of the polynucleotides to remove any undesired species (e.g., deoxynucleotides). In some embodiments, a polynucleotide construct comprises one or more adaptors which attach to the solid support, rendering the polynucleotide immobilized on the support. In some embodiments, the polynucleotide construct is immobilized on the surface of a flow cell or a glass slide. In some embodiments, the polynucleotide construct is immobilized on a microtitre well or magnetic bead. In some embodiments, the solid support may be coated with a polymer attached to a functional group or moiety. In some embodiments, the solid support may carry functional groups such as amino, hydroxyl, or carboxyl groups, or other moieties such as avidin or streptavidin for attachment of adaptors.

The polynucleotide constructs can comprise a binding partner, such as a biotin moiety, to facilitated enrichment or isolation of an insert. An insert can be attached to an adaptor comprising a binding partner, or an insert can be amplified using one or more primers comprising a binding partner. In some embodiments, the present methods comprise forming a complex between reciprocal binding partners, such as a biotinylated primer extension product and solid-supported avidin or streptavidin. The methods can also include enriching a sample containing the polynucleotide construct comprising a binding partner by binding to a reciprocal binding partner. The proteins avidin and streptavidin form exceptionally tight complexes with biotin and certain biotin analogs. In general, when biotin is coupled to a second molecule through its carboxyl side chain, the resulting conjugate is still tightly bound by avidin or streptavidin. The second molecule is said to be "biotinylated" when such conjugates are prepared. Useful binding partners include biotin:avidin, biotin:streptavidin, antibody:antigen, and complementary nucleic acids.

Preparation of polynucleotides for next generation sequencing often employs target enrichment prior to next-generation sequencing, and one or more target enrichment protocols can be included in the present methods. By enriching for one or more desired inserts, the sequencing can be more focused with reduced effort and expense and/or with high coverage depth. Examples of present enrichment protocols for next generation sequencing include hybridization-based capture protocols such as SureSelect Hybrid Capture from Agilent and TruSeq Capture from Illumina. Other examples include PCR-based protocols such as HaloPlex from Agilent; AmpliSeq from ThermoFisher; TruSeq Amplicon from Illumina; and emulsion/digital PCR from Raindance.

As discussed above, the polynucleotide constructs can be sequenced by primer extension. The primer extension determines sequence by detecting bases that are incorporated as a result of extension from the first primer, allowing the determination of at least a portion of an insert (or an identifier sequence in some embodiments) of the polynucleotide construct. The second primer extension determines sequence by detecting bases that are incorporated as a result of extension from the second primer, allowing for detection of the identifier (or an insert sequence, in some embodiments).

In some embodiments, sequencing is performed by sequencing-by-synthesis with reversible dye terminators as the labels. In some embodiments, sequencing is performed by sequencing-by-ligation. In some embodiments, sequencing is performed by single molecule sequencing. In some embodiments, sequencing is performed by pyrosequencing. The polynucleotide may be sequenced using any suitable reaction method. In some embodiments, a single reaction cycle may be done using a single nucleotide (i.e., a nucleotide corresponding to G, A, T or C) and the method involves detecting whether a nucleotide is incorporated. If a nucleotide is incorporated, then the identity of the nucleotide becomes known. In such embodiments, the method may involve cycling through all four nucleotides (i.e., nucleotides corresponding to G, A, T and C) in succession and one of the nucleotides should be incorporated. In such embodiments, the addition of the nucleotide may be detected by detecting pyrophosphate release, proton release or fluorescence, for example, methods for which are known. For example, in some embodiments, the chain terminator nucleotide may be a terminal phosphate labeled fluorescent nucleotide (i.e., a nucleotide that has a fluorophore attached to the terminal phosphate) and the identifying step comprises reading fluorescence. In other embodiments, the chain terminator nucleotide may be a fluorescent nucleotide that comprises a quencher on a terminal phosphate. In such embodiments, incorporation of the nucleotide removes the quencher from the nucleotide, thereby allowing the fluorescent label to be detected. In other embodiments, the terminal phosphate labeled chain terminator nucleotide may be labeled on the terminal phosphate with a mass tag, charge label, charge blockade label, chemiluminescent label, redox label, or other detectable label.

In some embodiments, a single reaction cycle may be done using all four nucleotides (i.e., nucleotides corresponding to G, A, T and C), each labeled with different fluorophores. In such embodiments, the sequencing step may comprises adding the four chain terminators corresponding to G, A, T and C to the amplified polynucleotide, wherein the four chain terminators comprise different fluorophores. In such embodiments, the identifying step may comprise identifying which of the four chain-terminator is added to the end of the primer.

The sequencing step can be performed using single-end sequencing, i.e., the first primer extension and the second primer extension sequences are read in the same direction. In some embodiments, a sequencing instrument that is configured for single-end sequencing is used to sequence the polynucleotide. In some embodiments, the method comprises continuously monitoring the sequencing reactions (i.e., nucleotide incorporation) in real time. This may simply be achieved by performing the primer extension and detection, or signal-generation, reactions simultaneously by including the "detection enzymes" in the chain extension reaction mixture. In some embodiments, the primer extension reaction is first performed separately as a first reaction step, followed by a separate "detection" reaction where the primer extension products are subsequently detected.

Example 1

In this example, various embodiments of the present methods of sequencing were performed without a denaturation step between insert sequencing and identifier sequencing. Polynucleotide constructs were prepared in the following manner: DNA was sheared with Covaris model E220, and end-repair, A-tailing, ligation and PCR amplication were performed with Agilent SureSelect XT HS target enrichment systems. The inserts used for this example were human genomic DNA (NA12878), and adaptors having sample identifiers were attached to known inserts, so that the association between insert sequences and identifier sequences was known and could be used to evaluate the experimental methods. The polynucleotide constructs were amplified by 12 rounds of PCR. The polynucleotide constructs were pooled for sequencing on a sequencing-by-synthesis instrument, in which the polynucleotide constructs attached to a flow cell. Primers, nucleotides and polymerases were added to the flow cell for primer extension reactions in accordance with normal operating procedures, except for the differences described below for the various experiments. The sequencing data was demultiplexed based on the identifier sequences, with insert sequences being assigned to sample groups based on their associated identifier sequences. Mismatches of insert sequences and identifier sequences were counted and used to evaluate performance of the sequencing methods.

Experiments A and B served as controls for the example, in that insert sequencing was performed with a first sequencing primer, resulting in the formation of a double-stranded insert portion, which comprises the insert and the complementary strand formed by the extension of the first primer with the labeled nucleotides in the course of sequencing. In accordance with existing methods, a denaturation step was carried out to separate the complementary strand from the insert prior to sequencing the identifier by extending a second primer with labeled nucleotides. In Experiments C and D, the insert was sequenced in the same way, but the complementary strand formed by extension of the first primer with the labeled nucleotides was not denatured before a second sequencing primer for the identifier was added and used for sequencing the identifier. The sequencing primer for the identifier (i.e., the second sequencing primer) was added after seventy sequencing cyclers were performed for insert sequencing. In Experiments E and F, the insert was sequenced for seventy sequencing cycles, then blocking nucleotides (2',3'-dideoxynucleotides) were added to the sequencing reaction to prevent continued extension of the double-stranded insert portion. The blocking nucleotides were then removed from the flow cell, and a sequencing primer for the identifier was introduced to the flow cell, along with labeled nucleotides. These experiments also did not denature the double-stranded insert portion before adding the second sequencing primer. Experiments G and H different from the other experiments in that the identifiers were sequenced first, then the inserts were sequenced; however, they are like Experiments C to F in that the double-stranded portion resulting from sequencing with the first primer was not denatured. In Experiments G and H, the first primer introduced to the flow cell was for sequencing the identifier, and it annealed to a primer binding site that was 3' to the insert. The identifier was sequenced with labeled nucleotides, resulting in the formation of a double-stranded identifier portion with a strand complementary to substantially all of the identifier. A second primer was added which annealed to a second primer binding site, which was 3' to the insert. In these polynucleotide constructs, the identifier is adjacent to the primer binding site for the insert. Before commencing the insert sequencing, the double-stranded identifier portion was ligated to the second primer, thereby removing any gap in the strand complementary to the initial polynucleotide construct. Labeled nucleotides were added, and a strand complementary to the insert was formed as the insert was sequenced.

Figure 5:
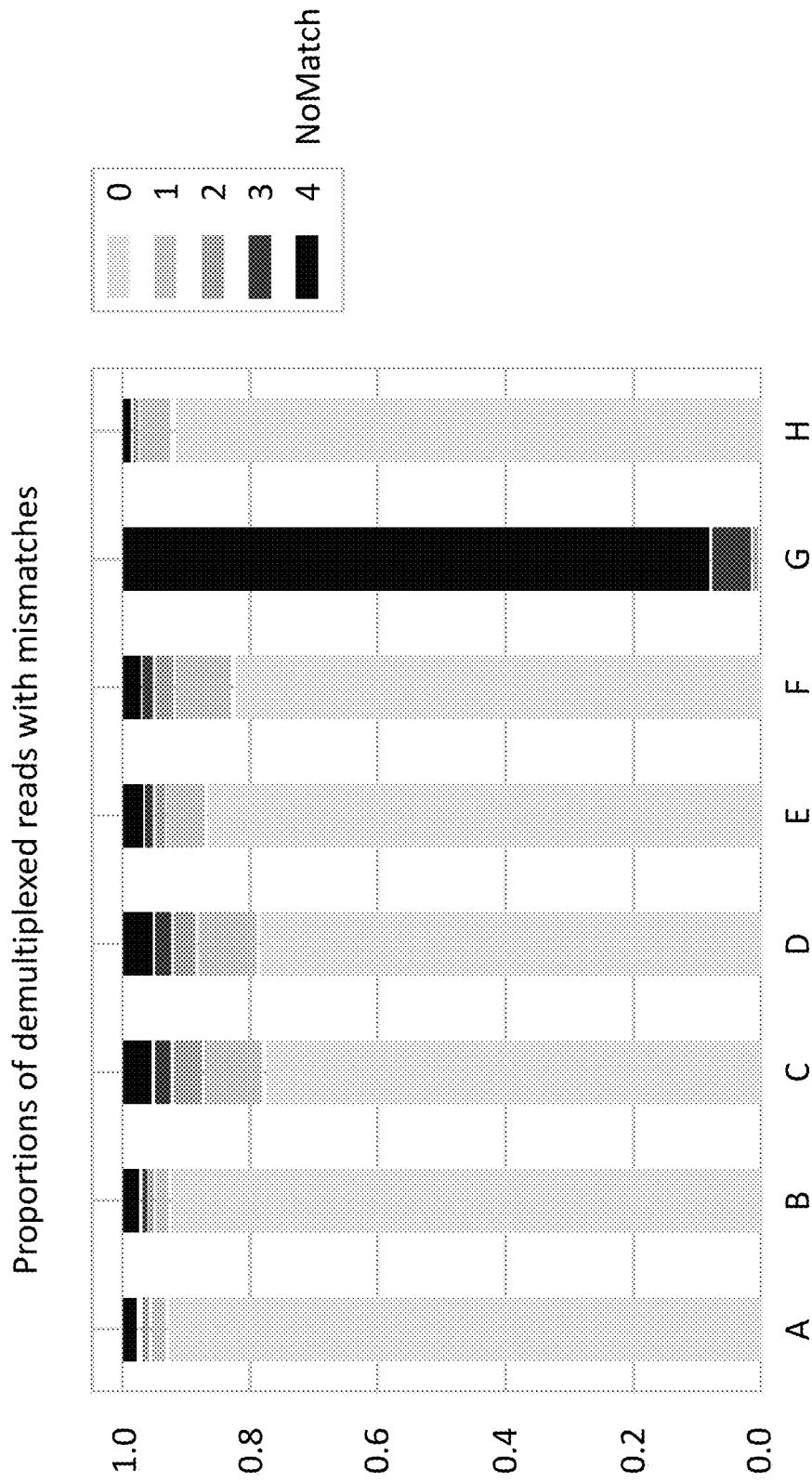
FIG. 5 illustrates performance data from several embodiments of the present sequencing methods.

The performance was evaluated based on proportions of sequencing reads with mismatches, and the results are summarized in FIG. 5. The control (Experiments A and B) produced 95.3-93.5% of reads with 0 or 1 mismatches. Experiments C and D produced 88.1-89.3% of reads 0 or 1 more mismatches. Experiments E and F produced 91.5-92.0% of reads with 0 or 1 mismatches. Experiment G failed for unknown reasons, but Experiment H indicated that ~98% (~97% in control) of reads can be demultiplexed with 2 or fewer mismatches.

Accordingly, these experiments demonstrate that the present sequencing methods can be used to generate high quality sequencing data for an insert and an identifier without a denaturation step between insert sequencing and identifier sequencing.

EXEMPLARY EMBODIMENTS

Embodiment 1. A method for sequencing an insert and an identifier in a polynucleotide construct, the method comprising: annealing a first primer to a region of the polynucleotide construct that is 3' to the insert, extending the first primer by addition of labeled nucleotides complementary to the insert, and detecting the added labeled nucleotides to determine a sequence of the insert, wherein the extension of the first primer forms a double-stranded insert portion comprising the insert and a strand complementary to the insert; annealing a second primer to a region of the polynucleotide construct that is 3' to the identifier; extending the second primer by addition of labeled nucleotides complementary to the identifier, and detecting the added labeled nucleotides to determine a sequence of the identifier, wherein the double-stranded insert portion is not denatured before annealing and extending the second primer.

Embodiment 2. The method of embodiment 1, wherein the method comprises extending the first primer and detecting the added labeled nucleotides for at least seventy sequencing cycles before annealing the second primer.

Embodiment 3. The method of embodiment 1, further comprising extending the double-stranded insert portion after the addition of the labeled nucleotides by adding unlabeled nucleotides until the complementary strand entirely extends over the insert.

Embodiment 4. The method of embodiment 1, further comprising adding a blocking nucleotide to the double-stranded insert portion after the addition of the labeled nucleotides.

Embodiment 5. The method of embodiment 4, wherein the blocking nucleotides are dideoxy nucleotides.

Embodiment 6. The method of any of the preceding embodiments, wherein the polynucleotide construct comprises a capture site, a first primer binding site for the first primer, an identifier, a second primer binding site for the second primer, and the insert.

Embodiment 7. The method of embodiment 6, wherein the identifier comprises a sample identifier, or a molecular identifier, or both.

Embodiment 8. The method of embodiment 6 or 7, wherein the first primer binding site is contiguous with the 5' end of the insert.

Embodiment 9. The method of any of embodiments 6, 7 or 8, wherein the second primer binding site is contiguous with a sample identifier or a molecular identifier.

Embodiment 10. A method for sequencing an insert and an identifier in a polynucleotide construct, the method comprising: annealing a first primer to a region of the polynucleotide construct that is 3' to the identifier; extending the first primer by addition of labeled nucleotides complementary to the identifier, and detecting the added labeled nucleotides to determine a sequence of the identifier, wherein the extension of the first primer forms a double-stranded identifier portion comprising the identifier and a strand complementary to the identifier; annealing a second primer adjacent to region of the polynucleotide construct that is 3' to the insert, extending the second primer by addition of labeled nucleotides complementary to the insert, and detecting the labeled nucleotides to determine a sequence of the insert, wherein the double-stranded identifier portion is not denatured before annealing and extending the second primer.

Embodiment 11. The method of embodiment 10, wherein the method comprises ligating the strand complementary to the identifier to the second primer before extending the second primer.

Embodiment 12. The method of embodiment 10, further comprising extending the double-stranded identifier portion after the addition of the labeled nucleotides by adding unlabeled nucleotides until the complementary strand extends over substantially all the identifier.

Embodiment 13. The method of embodiment 10, further comprising adding a blocking nucleotide to the double-stranded identifier portion after the addition of the labeled nucleotides.

Embodiment 14. The method of embodiment 13, wherein the blocking nucleotides are dideoxy nucleotides.

Embodiment 15. The method of any of embodiments 10 to 14, wherein the polynucleotide construct comprises a capture site, a first primer binding site for the first primer, an identifier, a second primer binding site for the second primer, and the insert.

Embodiment 16. The method of embodiment 15, wherein the identifier comprises a sample identifier, or a molecular identifier, or both.

Embodiment 17. The method of embodiment 15 or 16, wherein the identifier comprises a 5' end and a 3' end, and the first primer binding site is contiguous with the 5' end of the identifier.

Embodiment 18. The method of any of embodiments 15, 16 or 17, wherein the second primer binding site is contiguous with the 5' end of the insert.

Embodiment 19. A kit for sequencing a polynucleotide of interest, the kit comprising: one or more adaptors; one or more primers; labeled nucleotides; and one or both of (a) unlabeled nucleotides; and (b) blocking nucleotides.

Embodiment 20. The kit of embodiment 19 comprising blocking nucleotides, wherein the blocking nucleotides are dideoxy nucleotides.

In view of this disclosure it is noted that the methods can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

I claim:

1. A method for sequencing an insert and an identifier in a polynucleotide construct, the method comprising:
   annealing a first primer to a region of the polynucleotide construct that is 3' to the insert,
   extending the first primer by addition of labeled nucleotides complementary to the insert, and detecting the added labeled nucleotides to determine a sequence of the insert,
wherein the extension of the first primer forms a double-stranded insert portion comprising the insert and a strand complementary to the insert;
   annealing a second primer to a region of the polynucleotide construct that is 3' to the identifier;
wherein the first primer is extended and the added labeled nucleotides are detected for at least seventy sequencing cycles before annealing the second primer;
   extending the second primer by addition of labeled nucleotides complementary to the identifier, and detecting the added labeled nucleotides to determine a sequence of the identifier,
   wherein the double-stranded insert portion is not denatured before annealing and extending the second primer.

2. The method of claim 1, further comprising extending the double-stranded insert portion after the addition of the labeled nucleotides by adding unlabeled nucleotides until the complementary strand entirely extends over the insert.

3. The method of claim 1, wherein the polynucleotide construct comprises a capture site, a first primer binding site for the first primer, the identifier, a second primer binding site for the second primer, and the insert.

4. The method of claim 3, wherein the identifier comprises a sample identifier, or a molecular identifier, or both.

5. The method of claim 3, wherein the first primer binding site is contiguous with the 3' end of the insert.

6. The method of claim 3, wherein the second primer binding site is contiguous with the identifier.

7. A method for sequencing an insert and an identifier in a polynucleotide construct, the method comprising:
   annealing a first primer to a region of the polynucleotide construct that is 3' to the insert,
   extending the first primer by addition of labeled nucleotides complementary to the insert, and detecting the added labeled nucleotides to determine a sequence of the insert,
wherein the extension of the first primer forms a double-stranded insert portion comprising the insert and a strand complementary to the insert;
   adding a blocking nucleotide to the double-stranded insert portion after the addition of the labeled nucleotides;
   annealing a second primer to a region of the polynucleotide construct that is 3' to the identifier; and
   extending the second primer by addition of labeled nucleotides complementary to the identifier, and detecting the added labeled nucleotides to determine a sequence of the identifier,
   wherein the double-stranded insert portion is not denatured before annealing and extending the second primer.

8. The method of claim 7, wherein the blocking nucleotides are dideoxy nucleotides.

9. A method for sequencing an insert and an identifier in a polynucleotide construct, the method comprising:
   annealing a first primer to a region of the polynucleotide construct that is 3' to the identifier;
   extending the first primer by addition of labeled nucleotides complementary to the identifier, and detecting the added labeled nucleotides to determine a sequence of the identifier, wherein the extension of the first primer forms a double-stranded identifier portion comprising the identifier and a strand complementary to the identifier;
   annealing a second primer adjacent to region of the polynucleotide construct that is 3' to the insert,
   ligating the strand complementary to the identifier to the second primer before extending the second primer,
   extending the second primer by addition of labeled nucleotides complementary to the insert, and detecting the labeled nucleotides to determine a sequence of the insert,
   wherein the double-stranded identifier portion is not denatured before annealing and extending the second primer.

10. The method of claim 9, further comprising extending the double-stranded identifier portion after the addition of the labeled nucleotides by adding unlabeled nucleotides until the complementary strand extends over substantially all the identifier.

11. The method of claim 9, further comprising adding a blocking nucleotide to the double-stranded identifier portion after the addition of the labeled nucleotides.

12. The method of claim 11, wherein the blocking nucleotides are dideoxy nucleotides.

13. The method of claim 9, wherein the polynucleotide construct comprises a capture site, a first primer binding site for the first primer, the identifier, a second primer binding site for the second primer, and the insert.

14. The method of claim 13, wherein the identifier comprises a sample identifier, or a molecular identifier, or both.

15. The method of claim 13, wherein the identifier comprises a 5' end and a 3' end, and the first primer binding site is contiguous with the 3' end of the identifier.

16. The method of claim 13, wherein the second primer binding site is contiguous with the 3' end of the insert.

\* \* \* \* \*